United States Patent [19]
Zimmerman et al.

[11] Patent Number: 5,260,274
[45] Date of Patent: * Nov. 9, 1993

[54] FACTOR VIII BINDING DOMAIN OF VON WILLEBRAND FACTOR

[75] Inventors: Theodore S. Zimmerman, La Jolla; Paul A. Foster, San Diego; Carol A. Fulcher, La Jolla, all of Calif.

[73] Assignee: Scripps Clinic and Research Foundation, La Jolla, Calif.

[*] Notice: The portion of the term of this patent subsequent to Aug. 27, 2008 has been disclaimed.

[21] Appl. No.: 725,560

[22] Filed: Jul. 3, 1991

Related U.S. Application Data

[62] Division of Ser. No. 45,032, May 1, 1987, Pat. No. 5,043,429.

[51] Int. Cl.$^5$ .................... A61K 37/02; C07K 7/10
[52] U.S. Cl. .................................... 514/12; 514/2; 514/8; 514/13; 514/14; 514/15; 514/16; 514/17; 514/18; 530/325; 530/326; 530/327; 530/328; 530/329; 530/330; 530/331; 530/350; 530/380; 530/381; 530/383; 530/324

[58] Field of Search .............. 530/383, 350, 380, 381, 530/324, 325, 326, 327, 328, 329, 330, 331; 435/69.6, 68.1; 514/2, 8, 12, 21, 13, 14, 15, 16, 17, 18

[56] References Cited

U.S. PATENT DOCUMENTS 5,043,429 8/1991 Zimmerman et al. .............. 530/383

OTHER PUBLICATIONS

Titani, K. et al., *Biochemistry*, 25: 3174-3184, 1986.
Sadler, J. et al., *Proc. Natl. Acad. Sci.*, USA 82: 6394-6398, Oct. 1985.
Alberts et al., *Molecular Biology of the Cell*, Garland Publishing Inc., pp. 185-196, 1983.
Stewart et al., *Solid Phase Peptide Synthesis*, 2nd ed., Pierce Chemical Co., 1984.

*Primary Examiner*—Lester L. Lee
*Attorney, Agent, or Firm*—Morgan & Finnegan

[57] ABSTRACT

Peptides which inhibit the binding of von Willebrand Factor to Factor VIII. Monoclonal antibodies capable of specifically binding to the region of von Willebrand Factor containing the Factor VIII binding domain. Improved methods of preparing Factor VIII.

12 Claims, No Drawings

FACTOR VIII BINDING DOMAIN OF VON WILLEBRAND FACTOR

This invention was made with government support under Grant Numbers AM 07022, HL 35090 and HL 15491 awarded by The National Institute of Health. The government has certain rights in the invention.

This is a divisional of co-pending application Ser. No. 07/045,032 filed May 1, 1987 now U.S. Pat. No. 5,043,429.

BACKGROUND OF THE INVENTION

This invention relates to peptides which inhibit the binding of von Willebrand Factor (vWF) to Factor VIII (FVIII).

vWF and FVIII both have important but different functions in the maintenance of hemostasis. vWF participates in platelet-vessel wall interactions at the site of vascular injury whereas FVIII accelerates the activation of Factor X by Factor IXa in the presence of platelets and calcium ions. vWF and FVIII circulate in plasma as a noncovalently linked complex thought to be held together by both electrostatic and hydrophobic forces. vWF is thought to stabilize FVIII in vitro and prolong its half-life in the circulation. Consequently, in the absence of endogeneous vWF the circulating half-life of FVIII is markedly reduced. Since FVIII participates in the intrinsic Pathway of blood coagulation, agents capable of interfering with the interaction of FVIII and vWF would alter the FVIII level in plasma and in this manner serve as anti-thrombotic agents. The peptides of the present invention have the ability to act as anti-thrombotic agents by their prevention of the binding of vWF to FVIII. They also have the ability to stabilize FVIII in an in vitro environment in which FVIII is being produced.

SUMMARY OF THE INVENTION

The present invention comprises a 29 kDa polypeptide fragment selected from the following sequence:

3
|
SCRPPMVKLVCPADNLRAEGLECXKTCQNYDLECMSMGCVSGCLCPPGMVRHENRCVAL

ERCPCFHQGKEYAPGETVKIGCNTCVCRDRKWNCTDHVCDATCSTIGMAHYLTFDGLKYLFPG

ECQYVLVQDYCGSNPGTFRILVGNKGCSHPSVKCKKRVTILVEGGEIELFDGEVNVKRPMKDETH

FEVVESGRYIILLLGKALSVVWDRHLSISVVLKQTYQEKVCGLCGNFDGIQNNDLTSSNL

285
|
QVEEDPVDFGNSWKVSSQCADTRKVPLDSSPATCHN .

which inhibits binding of von Willebrand Factor to Factor VIII, whose amino acid sequence is that of a fragment of von Willebrand Factor and reacts with a monoclonal anti-vWF antibody C3 deposited with the American Type Culture Collection, 12301 Parklawn Drive, Rockville, Md. 20852 with the designation (ATCC No. HB 9425) capable of specifically binding to the region of von Willebrand Factor containing the Factor VIII binding domain.

Particularly preferred is a polypeptide which inhibits binding of von Willebrand Factor to Factor VIII wherein the polypeptide has the amino-terminal sequence beginning with amino-terminal amino acid residue 3 Ser and ending approximately with carboxy-terminal amino acid residue 244 Leu.

Additionally preferred is a polypeptide which inhibits binding of von Willebrand Factor to Factor VIII wherein the polypeptide has the amino-terminal sequence beginning with amino-terminal amino acid residue 24 Glu and ending approximately with carboxy-terminal amino acid residue 265 Ser.

Additionally preferred is a polypeptide which inhibits binding of von Willebrand Factor to Factor VIII wherein the polypeptide has the amino-terminal sequence beginning with amino-terminal acid residue 44 Gly and ending approximately with carboxy-terminal amino acid residue 285 Asn.

The invention further comprises a peptide comprising a sequential subset of at least three amino acid residues of a polypeptide fragment which inhibits binding of von Willebrand Factor to Factor VIII and reacts with a monoclonal anti-vWF antibody C3 capable of specifically binding to the region of von Willebrand Factor containing the Factor VIII binding domain and which has the following sequence:

3
|
SCRPPMVKLVCPADNLRAEGLECXKTCQNYDLECMSMGCVSGCLCPPGMVRHENRCVAL

ERCPCFHQGKEYAPGETVKIGCNTCVCRDRKWNCTDHVCDATCSTIGMAHYLTFDGLKYLFPG

ECQYVLVQDYCGSNPGTFRILVGNKGCSHPSVKCKKRVTILVEGGEIELFDGEVNVKRPMKDETH

FEVVESGRYIILLLGKALSVVWDRHLSISVVLKQTYQEKVCGLCGNFDGIQNNDLTSSNL

285
|
QVEEDPVDFGNSWKVSSQCADTRKVPLDSSPATCHN .

The invention further comprises a new mouse-mouse hybridoma cell line which provides as a component of the supernatant of its growth a monoclonal anti-vWF antibody C3 capable of specifically binding to the region of von Willebrand Factor containing the Factor VIII binding domain.

The invention further comprises a monoclonal anti-vWF antibody capable of specifically binding to the region of von Willebrand Factor containing the Factor VIII binding domain.

The invention further comprises an improved method of preparing Factor VIII by the addition of a polypeptide fragment and any sequential subset of at least three amino acids of the polypeptide fragment which inhibit binding of von Willebrand Factor to Factor VIII.

The invention further comprises an improved method of preparing Factor VIII using particles bound to a polypeptide fragment and any sequential subset of at least three amino acids of the polypeptide fragment which inhibit binding of von Willebrand Factor to Factor VIII.

The invention further comprises a method of preparing by recombinant DNA or synthetic peptide techniques a polypeptide fragment and any sequential subset of at least three amino acids of the polypeptide fragment which inhibit binding of von Willebrand Factor to Factor VIII.

The invention further comprises an improved method for expressing recombinant DNA produced Factor VIII using a polypeptide fragment and any sequential subset of at least three amino acids of the polypeptide fragment which inhibit binding of von Willebrand Factor to Factor VIII.

DETAILED DESCRIPTION OF THE INVENTION

As indicated the present invention encompasses polypeptide fragments and synthetic peptides which inhibit binding of vWF to FVIII, whose amino acid sequences are that of fragments of vWF and react with a monoclonal anti-vWF antibody C3 capable of specifically binding to the region of vWF containing the FVIII binding domain.

The monoclonal anti-vWF antibody C3 was found to have the ability to block the binding of purified human FVIII to purified human vWF in a crossed immunoelectrophoresis system. The epitope of C3 must reside close to that of the FVIII binding domain of vWF. The C3 antibody was therefore used as a marker of the FVIII binding domain.

Whole unreduced $^{125}$I-labeled vWF was treated with subtilisin at a 1/25 (w/w) ratio for 24 hours at room temperature. This reaction mixture was then placed in microtiter wells which had previously been coated with monoclonal anti-vWF antibody C3. The wells were thoroughly washed and then treated with SDS buffer heated to approximately 90° C. and the solution run on a 5-15% gradient SDS-PAGE gel. An autoradiograph of the SDS-PAGE gel demonstrated predominately a single band with a molecular weight of approximately 29 kDa. A similar digest of unlabeled vWF was made and this reaction mixture was placed on chromatography column made up of monoclonal anti-vWF antibody C3 coupled to Sepharose 4B. The C3 reactive fragments were then eluted with 3M NaSCN, dialyzed, and concentrated. A band reactive with C3 by immunoblotting techniques was identified. Amino acid sequencing of this band revealed that approximately 60% of the amino-termini began with amino acid residue number 44 of the mature vWF subunit, approximately 20% began with residue number 24 and approximately 10% began with residue number 3.

The above described experiment localized the C3 epitome and indirectly the FVIII binding domain to the amino-terminal region of vWF. Since the molecular weight of the peptide so identified was approximately 29 kDa and its predominant amino-terminus was amino acid residue 44 of the mature subunit, then the carboxy-terminus should be approximately at amino acid residue 285 based on an average molecular weight per amino acid residue of approximately 120. Based on the published amino acid sequence of vWF in Titani et al., Biochemistry 25, 3174-3184 (1986) it is possible to synthesize peptides from the region beginning with residue 3 and ending with amino acid residue 285 which comprises the region of vWF containing the FVIII binding domain.

In Titani et al. the sequence analysis identified both Ala, and Thr at a molar ratio of about 4:1 at residue 26. In contrast, the nucleotide sequence of the lambda HvWFl clone predicted Thr at residue 26 according to Sadler et al., Proc. Natl. Acad. Sci. USA 82, 6394-6398 (1985). This discrepancy can be due to polymorphism in the protein or to an error in cDNA replication during the preparation of the DNA library. In view of this uncertainty at residue 26, the amino acid at residue 26 is identified by X which represents an undetermined amino acid. These peptides can interfere with FVIII-vWF interaction and thus serve as antithrombotic agents. Additional monoclonal antibodies to this region can be produced which will also interfere with FVIII-vWF interaction and thus can also serve as anti-thrombotic agents.

Experimental procedures used in localizing the C3 epitope and indirectly the FVIII binding to the 29 kDa polypeptide fragment are explained in more detail below when these same procedures are used in localizing the C3 epitope and indirectly the FVIII binding to the 170 kDa polypeptide fragment.

The purification of FVIII from commercial factor VIII concentrate (Armour Pharmaceutical, Kankakee, Ill.), by immunoadsorbent chromatography with monoclonal anti-vWF antibody is described in Fulcher et al., Proc. Natl. Acad. Sci. USA 79, 1648-1652 (1982). FVIII preparations obtained by this method and used in the following experiments had specific activities of 2900-3800 units/mg. Purified vWF was obtained from commercial factor VIII concentrate (Armour Pharmaceutical, Kankakee, Ill.), by immunoadsorbent chromatography with a monoclonal anti-vWF antibody bound to Sepharose as described in Fulcher et al. The bound vWF was eluted by 3 M NaSCN as described in Fujimara et al., J. Biol. Chem. 261, 381-385 (1986) and concentrated and desalted with a tangential flow Minitan ultrafiltration system (Millipore, Bedford, Mass.), with a 100,000 molecular weight cut off membrane. The protein was further dialyzed extensively against 0.05 M Tris, 0.15 M NaCl, pH 7.35 (TBS).

Mouse monoclonal anti-FVIII and anti-vWF antibodies were produced, purified, and characterized and described in Fulcher et al. and Fujimara et al. Radioiodination of monoclonal anti-FVIII and anti-vWF antibodies were done according to the method of Fraker and Speck, Biochem. Biophys. Res. Commun. 80, 849-857 (1978), to a specific activity of 3-10 $\times 10^9$ cpm/mg.

SP fragment-III was obtained by limited proteolysis of vWF with *Staphylococcus aureus* V8 protease (Sigma, St. Louis, Mo.), and purified by the method of Girma et al., Biochemistry 25, 3156-3163 (1986), with modifications as described by Titani et al., Biochemistry 25, 3171-3184. All fragments were dialyzed against TBS pH 7.35 before testing.

The reduction and alkylation of vWF was performed as has been previously described in Fujimara et al.

Two dimensional crossed immunoelectrophoresis of vWF was performed as described in Zimmerman et al., Immunoassays: Clinical Laboratory Techniques for the 1980's, pp. 339-349, Alan R. Liss, Inc., New York (1980), with the following modifications. Agarose was poured in a 1.5 cm strip at the bottom of a 10.2 cm×8.3 cm piece of Gelbond (FMC Corporation, Rockland, Me.). Purified vWF or fragments of vWF, FVIII, and $^{125}$I labeled monoclonal anti-FVIII antibody were mixed in the sample well and electrophoresed. A second gel containing 125-250 μl of rabbit serum containing polyclonal anti-vWF antibodies was then poured and the second dimension was electrophoresed at right angles to the first dimension. Autoradiographs were made of the gels and compared to Coomassie brilliant blue staining of the gels.

Competitive inhibition assay of FVIII binding to solid phase vWF: 50 μg of whole unreduced vWF in 1 ml of 0.01 M PO., 0.15 M NaCl, 0.02% NaN$_3$, pH 7.3 (PBS), was incubated with three ¼ inch in diameter polystyrene beads (Pierce Chemical Company, Rockford, Ill.) per 16 mm in diameter tissue culture well for 2 hours at room temperature. The solution was removed and the wells and the beads were then blocked with 1 ml of PBS containing 0.05% Tween-20 and 3% human serum albumin for 1 hour at room temperature. The wells and the beads were stored in the blocking solution at 4° C. for 16 hours to 10 days before use. The wells and beads were then washed ×3 with PBS 0.05% Tween-20 and incubated for 1½ hours at room temperature with 1.3 μg of purified FVIII and 0-100 μg of the competitive ligand in 1 ml of 0.05 M imidazole, 0.15 M NaCl, 0.02% NaN$_3$, pH 7.0, 3 mM CaCl. The beads then were washed ×5 with PBS 0.05% Tween-20 and incubated for 1½ hour at room temperature with 1.5×10$^6$ cpm of $^{125}$I-monoclonal anti-FVIII antibody C2 (specific activity 3.8×10$^9$ cpm/mg), in 1 ml of PBS 0.05% Tween-20 containing 0.5% bovine gamma globulin. After incubation, the wells and beads were washed with PBS 0.05% Tween-20×2. The beads were then transferred to clean wells and washed an additional four times and separately counted. Total cpm in the absence of competing ligands ranged from 1340-2520 cpm in different experiments Background counts were those obtained when $^{125}$I-monoclonal anti-FVIII antibody C2 was incubated with the vWF coated beads in the absence of FVIII. These ranged from 60-200 cpm.

Protein concentrations were determined by the method of Bradford, Anal. Biochem. 72:248-254 (1976), using bovine serum albumin as a standard.

Crossed immunoelectrophoresis demonstrated complex formation between purified vWF and purified FVIII. This was shown by co-precipitation of $^{125}$I-labeled monoclonal anti-FVIII antibody with unlabeled vWF only when purified FVIII was included in the sample well. In order to localize the FVIII binding domain, similar experiments were performed with vWF fragments obtained by *Staphylococcus aureus* V8 protease digestion. Limited digestion of vWF with *Staphylococcus aureus* V8 protease has been reported to produce primarily a single cleavage in vWF yielding two major fragments. SP fragment II is a 110-kDa homodimer containing the carboxy-terminal portion of the vWF molecule (residues 1366-2050) and SP fragment III is a 170-kDa homodimer containing the amino-terminal portion of the vWF molecule. This 170-kDa polypeptide fragment has an amino-terminal sequence beginning with amino-terminal amino acid residue 1 Ser and a carboxy-terminal amino acid residue extending no further than amino acid residue 1365-Glu according to the amino acid sequence published in Titani et al., Biochemistry, 25, 3171-3184 (1986). These two fragments represent 100% of the molecular mass of the vWF subunit. Complex formation was demonstrated between FVIII and the amino-terminal SP fragment III but not with the carboxy-terminal SP fragment II. This indicates that the amino-terminal SP fragment III in its homodimeric form maintains the capability of interaction with FVIII in a qualitatively similar way as that of whole vWF. The carboxy-terminal SP fragment II in its homodimeric form does not demonstrate this FVIII binding capability.

The monoclonal anti-vWF antibody C3 largely inhibited complex formation between FVIII and vWF when it was included in the sample well, whereas 80 other monoclonal anti-vWF antibodies (tested in pools of 5 each) were without effect. C3 also inhibited complex formation between FVIII and SP fragment III in this system. Direct reactivity of C3 with SP fragment III was shown by adding $^{125}$I-labeled C3 to a sample well containing Purified SP fragment III. Autoradiographs of the crossed immunoelectrophoresis gel showed co-precipitation of the radiolabeled antibody with SP fragment III. In a similar experiment, no co-precipitation with SP fragment II occurred.

In order to better characterize FVIII binding to vWF, a competitive inhibition assay was developed. In this assay purified vWF or SP fragment III was adsorbed to the surface of polystyrene beads. The beads were then incubated with purified FVIII. Purified FVIII bound to both unreduced vWF and unreduced SP fragment III which had been immobilized on the surface of the polystyrene beads. This was demonstrated by the binding of $^{125}$I-labeled monoclonal anti-FVIII antibody to polystyrene beads sequentially incubated with vWF and FVIII.

Both the binding of FVIII to vWF and the binding of $^{125}$I-labeled monoclonal anti-FVIII antibody to FVIII were specific in this system as demonstrated by the following experiments. First, the binding of FVIII was shown to be dependent on the presence of vWF adsorbed to the surface of the polystyrene beads. When the polystyrene beads were coated with human serum albumin and then incubated with FVIII, followed by $^{125}$I-labeled monoclonal anti-FVIII antibody, the counts per minute measured were only 2% of that seen with FVIII binding to vWF coated polystyrene beads. Secondly, when vWF coated polystyrene beads were not incubated with FVIII, the bead associated counts per minute were only 1% of that seen when the FVIII incubation was included The reversibility of the binding of FVIII to the immobilized vWF could also be demonstrated. Dissociation of FVIII from the vWF-FVIII complex has been shown to occur in the presence of 0.25 M CaCl$_2$ according to Cooper et al., J. Clin. Invest. 54, 1093-1094 (1974), 10-20 mM EDTA according to Tran et al., Thromb. Haemostas. 50, 547-551 (1983) or 1-1.5 M NaCl according to Weiss et al., Thromb. Diath. Haemorrh. 27, 212-219 (1972). In the polystyrene bead system, five washings of the polystyrene beads with an imidazole buffered saline containing 0.25 M CaCl$_2$ at 37° C. produced 70+/−4% dissociation of FVIII from vWF. Similarly, five washings with an imidazole buffered saline containing 20 mM EDTA produced 66+/−5% dissociation and with an imidazole buffer containing 1.5 M NaCl produced 86 +/−1% dissociation of FVIII from vWF. Five washings with the same imidazole buffered saline containing 3 mM CaCl$_2$ produced no FVIII dissociation from vWF adsorbed to the polystyrene beads.

The specificity of the binding of fluid phase FVIII to vWF immobilized to the surface of the polystyrene beads was also shown by the ability of whole, unreduced vWF in fluid phase to completely inhibit this binding. Reduced and alkylated vWF had no inhibitory effect on FVIII binding. Reduced and alkylated vWF, and reduced and alkylated SP fragment III, were also unable to bind FVIII in the crossed immunoelectrophoresis system. These findings are consistent with the observation that under mild reducing conditions FVIII can be dissociated from vWF, see Blomback et al., Thromb. Res. 12, 1177–1194 (1978).

SP fragment III demonstrated dose dependent inhibition of FVIII binding with 90% inhibition at a concentration of 50 μg/ml. SP fragment I, a product of *Staphylococcus aureus* V8 protease digestion of SP fragment III which contains the middle portion of the vWF molecule (residues 911–1365 as described in Titani et al., Biochemistry 25, 3171–3184 (1986)) produced only 15% inhibition at concentrations up to 100 μg/ml. These data localized a major FVIII binding domain to the amino-terminal portion of vWF. SP fragment II inhibited FVIII binding by 29% at a concentration of 50 μg/ml. Doubling the concentration produced no significant increase in inhibition.

The complete 2050 amino acid sequence of vWF has been determined by protein sequence analysis, see Titani et al., Biochemistry 25, 3171–3184 (1986). With such information a nucleotide sequence can be inserted into the appropriate vector for expression of the 29 kDa and 170 kDa polypeptide fragments and sequential subsets of polypeptide fragments which inhibit binding of vWF to FVIII. For a description of recombinant DNA techniques for cloning vWF fragments, see Ginsburg et al., Science 228:1401–1406 (1985) and Sadler et al., Proc. Nat. Acad. Sci. USA 82, 6394–6398 (1985).

Peptides at least three amino acid residues in length beginning from the amino-terminal region of the 29 kDa polypeptide fragment are synthesized as described by Houghton et al., Proc Natl. Acad. Sci. USA 82:5135 (1985).

In the well known procedure for solid-phase synthesis of a peptide, the desired peptide is assembled starting from an insoluble support such as benzhydryl amine or chloromethylated resin (derived from cross-linked polystyrene, and available from chemical supply houses). The amino acid at the carboxy-terminal end of the desired polypeptide, carrying protecting groups on the alpha-amino nitrogen and on any other reactive sites, is attached to the resin from solution using known peptide coupling techniques. The protecting group on the alpha-amino group is removed (leaving other protecting groups, if any, intact), and the next amino acid of the desired sequence (carrying suitable protecting groups) is attached, and so on. When the desired polypeptide has been completely built up, it is cleaved from the resin support, all protecting groups are removed, and the polypeptide is recovered. Examples of suitable protecting groups are: alpha-tert-butyloxycarbonyl for the alpha-amino-group; benzyl, 4-methoxybenzyl, or 4-methylbenzyl for the thiol group of cysteine, the beta-carboxylic acid group of aspartic acid, the gamma-carboxylic acid group of glutamic acid and the hydroxyl groups of serine, threonine, and tyrosine; benzyloxycarbonyl or a 2-chloro- or 3, 4-dimethoxy-derivative thereof for the ring nitrogens of histidine and tryptophan and the epsilon-amino group of lysine; p-nitrophenyl for the amide nitrogens of asparagine and glutamine; and nitro or tosyl for the guanidine group of arginine.

For purposes of this disclosure, accepted short-hand designations of the amino acids have been used. A complete listing is provided herein below:

One and Three-letter Amino Acid Abbreviations

| | | |
|---|---|---|
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Glu | Glutamine |
| R | Arg | Arginine |
| S | Ser | Serine |
| T | Thr | Threonine |
| V | Val | Valine |
| W | Trp | Tryptophan |
| Y | Tyr | Tyrosine |
| B | Asx | Asp or Asn, not distinguished |
| Z | Glx | Glu or Gln, not distinguished |
| X | X | Undetermined or atypical amino acid |

One or more of the peptides of the present invention can be formulated into pharmaceutical preparations for therapeutic, diagnostic, or other uses. To prepare them for intraveneous administration, the compositions are dissolved in water containing physiologically compatible substances such as sodium chloride (e.g. 0.35–2.0 M), glycine, and the like and having a buffered pH compatible with physiological conditions. The amount to administer for the prevention of thrombosis will depend on the severity with which the patient is subject to thrombosis, but can be determined readily for any particular patient.

The following example is given as illustrative of the present invention. The present invention is not restricted only to this example.

EXAMPLE 1

Preparation of monoclonal antibody, C3, from hybridoma cell line

In the procedure for production of the hybridoma cell line producing monoclonal anti-vWF antibody C3 mice of strain BALB/c (Research Institute of Scripps Clinic) were immunized intraperitoneally with purified FVIII immunogen containing small amounts of vWF which co-purified with it as a contaminant. The FVIII was prepared as described in Fulcher et al., Proc. Natl. Acad. Sci. USA 79, 1648–1652 (1982). The mice were immunized intraperitoneally with 1 μg of immunogen in complete Freund's adjuvant. Seven days later the mice were immunized intraperitoneally with 10 μg of immunogen in incomplete Freund's adjuvant. Seven days after this second injection they were immunized intraperitoneally with 50 μg of immunogen in incomplete Freund's adjuvant. Eight days after this third injection they were immunized intraperitoneally with 100 μg of soluble immunogen. Spleens were removed three days later, and spleen cells were fused with P3x63-AG8.653 (mouse myeloma cell line).

P3X653-AG8.653 was maintained (before fusion) at log phase growth in a medium of 90% Dulbecco's modified Eagle's medium (high glucose) and 10% Fetal bovine serum (FBS). The following recommended supplements were added to 475 ml of the above medium: glutamine (100×) 5 ml, sodium pyruvate (100×) 5 ml, nonessential amino acids (100×) 5 ml, Pen-strep-fungizone (100×) 5 ml and 8-azaguanine 6.6×10$^{-3}$ M (50×) 10 ml. Spleen and myeloma cells were washed thoroughly without FBS in Dulbecco's modified Eagle's medium before fusion. Cells were fused with 1 ml 40% PEG 1500 for 1 minute. Then cells were diluted 1:2 with growth medium for 1 minute. Cells were diluted further 1:5 with growth medium for 2 minutes. Next cells were spun 900 RPM for 10 minutes. The supernatant was removed, the cells were selected by suspension in HAT medium and placed in 96 well plates. The HAT medium contained 90% Dulbecco's modified Eagle's medium (high glucose), 10% FBS and the following recommended supplements added to 405 ml of the above two components: glutamine (100×) 5 ml, NCTC 109 50 ml, sodium pyruvate (100×) 5 ml, nonessential amino acids (100×) 5 ml, Pen-strep-fungizone (100×) 5 ml, (hypoxanthine 10$^{-2}$ M+thymidine 1.6×10$^{-3}$ M) (100×) 5 ml, bovine insulin (20 I.U./ml)(100×) 5 ml, oxaloacetate (10$^{-1}$ M) (100×) 5 ml and aminopterin (2×10$^{-5}$ M)(50×) 10 ml. For 4 weeks following selection the cells were maintained in growth medium—HT (selection medium minus aminopterin). Subcloning was accomplished by limiting dilution. Wells with growth are tested by ELISA assay. Test plates were coated with 100 ng/well immunogen or human fibrinogen, or human fibronectin, or human vWF, each protein being a potential contaminant of the immunogen. 50 μg of culture supernatant were tested. Those wells containing cells whose supernatants were positive with a vWF were grown at 37° C. in 10% CO$_2$.

For ascites production the mice were primed with 0.5 ml pristine at least 4 days before cell injection. The cells were injected intraperitoneally (5×10$^6$/mouse) in 0.5 ml media with no FBS. The ascites were harvested when the mice bloated. The monoclonal anti-vWF antibody C3 contained in the mouse ascites is of the IgG-1 type.

The following Protein A sepharose purification of monoclonal anti-vWF antibody C3 from mouse ascites is a modified procedure of that disclosed in Ey et al. Immunochemistry, 15, 429-436 (1978). The amounts used were for a column 1 cm×15 cm which bound about 25-30 mg IgG-1, but which allowed separation of about 50 mg IgG-1 from non-IgG proteins. The column can also bind 50 mg of IgG2a. IgG2b also binds to the column, but IgM, IgA and IgE do not bind. 4-6 ml of ascites was centrifuged at 30,000 rpm for 45 minutes. The lipids were removed on top. The addition of 20% sucrose weight/column to the ascites aided in the removal of lipids. Ascites was diluted to 25-30 ml with 140 mM NaPO. buffer, PH8, containing 0.02% NaN$_3$. The ascites was diluted to prevent the interference of chloride ion with the binding of IgG. Approximately 2 g of Protein A sepharose (Sigma) was 16 swollen in 10 mM phosphate buffered saline with 0.02% NaN$_3$ and packed into a 1 cm diameter column. The column was equilibrated in 140 mM NaPO$_4$ buffer with 0.02% NaN$_3$. The column was loaded with diluted ascites at 0.06-0.08 ml/min or less. The column was allowed to sit at 4° C. overnight after loading to increase binding of IgG. The column was washed with buffers at 0.6-0.8 ml/min in the following order:

1) 140 mM NaPO$_4$, pH 8.0; 2) 0.1 M Na citrate - citric acid, pH 6.0 (IgG-1 eluted); 3) 0.1 M Na citrate-citric acid, pH 5.0 - IgG2a eluted and a small percentage of remaining IgG-1; 4) 0.1 M Na citrate-citric acid (small percentage of remaining IgG2a eluted); and 5) 0.1 M Na citrate-citric acid, pH 3.0 (IgG2b eluted). As soon as the column was washed with pH 3.0 buffer, it was washed with 140 mM NaPO$_4$ buffer, pH 8.0+0.02% NaN$_3$ until pH of effluent is 8.0. The column was stored at 4° C. During the washing of the column approximately 5 ml fractions were collected. To any fraction of pH 5.0, 1 ml of 1 M tris HCl was added.

What is claimed is:

1. A method of inhibiting the binding of vWF to Factor VIII comprising binding an effective amount of one or more polypeptides to Factor VIII, said polypeptides having an amino acid sequence which is a sequential subset of the following sequence:

3
|
SCRPPMVKLVCPADNLRAEGLECXKTCQNYDLECM

SMGCVSGCLCPPGMVRHENRCVAL

ERCPCFHQGKEYAPGETVKIGCNTCVCRDRKWN

CTDHVCDATCSTIGMAHYLTFDGL

KYLFPGECQYVLVQDYCGSNPGTFRILVGNKGCS

HPSVKCKKRVTILVEGGEIELFDGE

VNVKRPMKDETHFEVVESGRYIILLLGKALSVVW

DRHLSISVVLKQTYQEKVCGLCGN

FDGIQNNDLTSSNLQVEEDPVDFGNSWKVSSQCA

285
|
DTRKVPLDSSPATCHN wherein the N-terminal amino acid of said polypeptide is selected from amino acid 3(Ser) through 44(Gly) of said sequence and the C-terminal amino acid of said polypeptide is selected from about amino acid 244 (leu) through 285 (Asp) of said sequence, said polypeptide further characterized by its ability to inhibit binding of von Willebrand Factor to Factor VIII.

2. A method of inhibiting the binding of vWF to Factor VIII comprising binding an effective amount of one or more polypeptides with Factor VIII, said polypeptides consisting essentially of the amino acid sequence:

3
|
SCRPPMVKLVCPADNLRAEGLECXKTCQNYDLECMSMGCVSGCLCPPGMVRHENRCV

ALERCPCFHQGKEYAPGETVKIGCNTCVCRDRKWNCTDHVCDATCSTIGMAHYLTFD

GLKYLFPGECQYVLVQDYCGSNPGTFRILVGNKGCSHPSVKCKKRVTILVEGGEIELFD

GEVNVKRPMKDETHFEVVESGRYIILLLGKALSVVWDRHLSISVVLKQTYQEKVCGLC

GNFDGIQNNDLTSSNLQVEEDPVDFGNSWKVSSQCADTRKVPLDSSPATCHN[285].

3. A pharmaceutical composition for preventing thrombosis comprising an effective amount of one or more polypeptides in a pharmaceutically acceptable carrier, said polypeptides having an amino acid sequence which is a sequential subset of the following sequence:

[3]SCRPPMVKLVCPADNLRAEGLECXKTCQNYDLECMSMGCVSGCLCPPGMVRHENRCV

ALERCPCFHQGKEYAPGETVKIGCNTCVCRDRKWNCTDHVCDATCSTIGMAHYLTFD

GLKYLFPGECQYVLVQDYCGSNPGTFRILVGNKGCSHPSVKCKKRVTILVEGGEIELFD

GEVNVKRPMKDETHFEVVESGRYIILLLGKALSVVWDRHLSISVVLKQTYQEKVCGLC

GNFDGIQNNDLTSSNLQVEEDPVDFGNSWKVSSQCADTRKVPLDSSPATCHN[285].

4. A pharmaceutical composition for preventing thrombosis comprising an effective amount of a polypeptide in a pharmaceutically acceptable carrier, said polypeptide consisting essentially of the amino acid sequence:

[3]SCRPPMVKLVCPADNLRAEGLECXKTCQNYDLECM

SMGCVSGCLCPPGMVRHENRCVAL

ERCPCFHQGKEYAPGETVKIGCNTCVCRDRKWN

CTDHVCDATCSTIGMAHYLTFDGL

KYLFPGECQYVLVQDYCGSNPGTFRILVGNKGCS

HPSVKCKKRVTILVEGGEIELFDGE

VNVKRPMKDETHFEVVESGRYIILLLGKALSVVW

DRHLSISVVLKQTYQEKVCGLCGN

FDGIQNNDLTSSNLQVEEDPVDFGNSWKVSSQCA

DTRKVPLDSSPATCHN[285]

wherein the N-terminal amino acid of said polypeptide is selected from amino acid 3(Ser) through 44(Gly) of said sequence and the C-terminal amino acid of said polypeptide is selected from about amino acid 244 (Leu) through 285 (Asp) of said sequence, said polypeptide further characterized by its ability to inhibit binding of von Willebrand Factor to Factor VIII.

5. The pharmaceutical composition of claim 3 wherein the pharmaceutically acceptable carrier has a physiologically acceptable pH and comprises 0.35–2.0 M sodium chloride and glycine.

6. The pharmaceutical composition of claim 4 wherein the pharmaceutically acceptable carrier has a physiologically acceptable pH and comprises 0.35–2.0 M sodium chloride and glycine.

7. A method of preventing thrombosis which comprises the intravenous administeration of an effective amount of the pharmaceutical composition of claim 3.

8. A method of preventing thrombosis which comprises the intravenous administeration of an effective amount of the pharmaceutical composition of claim 4.

9. A method of preventing thrombosis which comprises the intravenous administration of an effective amount of the pharmaceutical composition of claim 5.

10. An isolated and substantially pure von Willebrand polypeptide consisting essentially of the amino acid sequence:

[44]GCLCPPGMVRHENRCVALERCPCFHQGKEYAPGETVKIGCNTCVCRDRKWNCTDHVC

DATCSTIGMAHYLTFDGLKYLFPGECQYVLVQDYCGSNPGTFRILVGNKGCSHPSVKC

KKRVTILVEGGEIELFDGEVNVKRPMKDETHFEVVESGRYIILLLGKALSVVWDRHLSIS

VVLKQTYQEKVCGLCGNFDGIQNNDL[244]

11. A method of inhibiting the binding of vWF to Factor VIII comprising binding an effective amount of the polypeptide of claim 10 to Factor VIII.

12. A pharmaceutical composition for preventing thrombosis comprising an effective amount of the polypeptide of claim 10 in a pharmaceutically acceptable carrier.

* * * * *

REEXAMINATION CERTIFICATE (3425th)

United States Patent [19]
Zimmerman et al.

[11] B1 5,260,274
[45] Certificate Issued *Jan. 20, 1998

[54] FACTOR VIII BINDING DOMAIN OF VON WILLEBRAND FACTOR

[75] Inventors: Theodore S. Zimmerman, La Jolla; Paul A. Foster, San Diego; Carol A. Fulcher, La Jolla, all of Calif.

[73] Assignee: The Scripps Research Institute, La Jolla, Calif.

Reexamination Request:
No. 90/004,577, Mar. 7, 1997

Reexamination Certificate for:
Patent No.: 5,260,274
Issued: Nov. 9, 1993
Appl. No.: 725,560
Filed: Jul. 3, 1991

[*] Notice: The portion of the term of this patent subsequent to Aug. 27, 2008, has been disclaimed.

Related U.S. Application Data

[62] Division of Ser. No. 45,032, May 1, 1987, Pat. No. 5,043,429.

[51] Int. Cl.$^6$ .................... A61K 38/36; C07K 14/745
[52] U.S. Cl. .................... 514/12; 514/2; 514/8; 514/13; 514/14; 514/15; 514/16; 514/17; 514/18; 530/324; 530/325; 530/326; 530/327; 530/328; 530/329; 530/330; 530/331; 530/350; 530/380; 530/381; 530/383

[58] Field of Search .................... 530/324, 325, 530/326, 327, 328, 329, 330, 331, 350, 380, 381, 382, 383; 435/68.1, 69.1; 514/2, 8, 12, 13, 14, 15, 16, 17, 18, 21

[56] References Cited

U.S. PATENT DOCUMENTS 5,043,429  8/1991  Zimmerman et al. .................... 530/383

OTHER PUBLICATIONS

Titani, K. et al, "Amino Acid Sequence of Human von Willebrand Factor", *Biochemistry*, 25:3174–3184, 1986.

Sadler, J. et al, "Cloning and characterization of two cDNAs coding for human von Willebrand factor", *Proc. Natl. Acad. Sci. USA* 82:6394–6398, Oct. 1985.

Hamilton et al, *J. Clin. Investigation*. vol. 76, No. 1, pp. 261–270 (Jul.) 1985.

Alberts et al, *Molecular Biology of the Cell*, Garland Publishing Inc., pp. 185–196, 1983.

Stewart et al, *Solid Phase Peptide Synthesis*, 2nd ed., Pierce Chemical Co., 1984.

*Primary Examiner*—Jeffrey Edwin Russel

[57] ABSTRACT

Peptides which inhibit the binding of von Willebrand Factor to Factor VIII. Monoclonal antibodies capable of specifically binding to the region of von Willebrand Factor containing the Factor VIII binding domain. Improved methods of preparing Factor VIII.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–3, 5, 7 and 9 is confirmed.

Claims 4, 6, 10 and 11 are determined to be patentable as amended.

Claims 8 and 12, dependent on an amended claim, are determined to be patentable.

New claim 13 is added and determined to be patentable.

4. A pharmaceutical composition for preventing thrombosis comprising an effective amount of a polypeptide in a pharmaceutically acceptable carrier, said polypeptide consisting [essentially] of the amino acid sequence:

3
|
SCRPPMVKLVCPADNLRAEGLECXKTCQNYDLECMSMGCVSGCL

CPPGMVRHENRCVALERCPCFHQGKEYAPGETVKIGCNTCVCRDR

KWNCTDHVCDATCSTIGMAHYLTFDGLKYLFPGECQYVLVQDYC

GSNPGTFRILVGNKGCSHPSVKCKKRVTILVEGGEIELFDGEVNVK

RPMKDETHFEVVESGRYIILLLGKALSVVWDRHLSISVVLKQTYQ

EKVCGLCGNFDGIQNNDLTSSNLQVEEDPVDFGNSWKVSSQCAD

285
|
TRKVPLDSSPATCHN .

6. [The] A pharmaceutical composition [of claim 4] *for preventing thrombosis comprising an effective amount of a polypeptide in a pharmaceutically acceptable carrier, said polypeptide consisting essentially of the amino acid sequence:*

3
|
SCRPPMVKLVCPADNLRAEGLECXKTCQNYDLECMSMGCVSGCL

CPPGMVRHENRCVALERCPCFHQGKEYAPGETVKIGCNTCVCRDR

KWNCTDHVCDATCSTIGMAHYLTFDGLKYLFPGECQYVLVQDYC

GSNPGTFRILVGNKGCSHPSVKCKKRVTILVEGGEIELFDGEVNVK

RPMKDETHFEVVESGRYIILLLGKALSVVWDRHLSISVVLKQTYQ

EKVCGLCGNFDGIQNNDLTSSNLQVEEDPVDFGNSWKVSSQCAD

285
|
TRKVPLDSSPATCHN wherein the pharmaceutically acceptable carrier has a physiologically acceptable pH and comprises 0.35–2.0M sodium chloride and glycine.

10. An isolated and substantially pure von Willebrand polypeptide consisting [essentially] of the amino acid sequence:

44
|
GCLCPPGMVRHENRCVALERCPCFHQGKEYAPGETVKIGCNTCVC

RDRKWNCTDHVCDATCSTIGMAHYLTFDGLKYLFPGECQYVLVQ

DYCGSNPGTFRILVGNKGCSHPSVKCKKRVTILVEGGEIELFDGEV

NVKRPMKDETHFEVVESGRYIILLLGKALSVVWDRHLSISVVLKQ

244
|
TYQEKVCGLCGNFDGIQNNDL .

11. A method of inhibiting the binding of vWF to Factor VIII comprising binding an effective amount of [the] *an isolated and substantially pure von Willebrand* polypeptide [of claim 10] to Factor VIII, *said polypeptide consisting essentially of the amino acid sequence:*

44
|
GCLCPPGMVRHENRCVALERCPCFHQGKEYAPGETVKIGCNTCVC

RDRKWNCTDHVCDATCSTIGMAHYLTFDGLKYLFPGECQYVLVQ

DYCGSNPGTFRILVGNKGCSHPSVKCKKRVTILVEGGEIELFDGEV

NVKRPMKDETHFEVVESGRYIILLLGKALSVVWDRHLSISVVLKQ

244
|
TYQEKVCGLCGNFDGIQNNDL .

*13. A method of preventing thrombosis which comprises the intravenous administration of an effective amount of the pharmaceutical composition of claim 6.*

* * * * *